United States Patent [19]

Nord

[11] Patent Number: 4,573,914
[45] Date of Patent: Mar. 4, 1986

[54] FORMATIVE ORTHODONTIC APPLIANCE

[76] Inventor: Philip J. Nord, 5213 SE. 30th #210A, Portland, Oreg. 97202

[21] Appl. No.: 695,706

[22] Filed: Jan. 28, 1985

[51] Int. Cl.$^4$ .............................................. A61C 3/00
[52] U.S. Cl. .......................................... 433/18; 433/7; 433/23
[58] Field of Search .................. 433/18, 19, 20, 22, 433/23, 17, 7, 6

[56] References Cited

U.S. PATENT DOCUMENTS

| | | | |
|---|---|---|---|
| 626,476 | 6/1899 | Angle | 433/20 |
| 3,798,773 | 3/1974 | Northcutt | 433/19 |
| 4,431,411 | 2/1984 | Witzig et al. | 433/6 |
| 4,433,956 | 2/1984 | Witzig | 433/7 |
| 4,468,196 | 8/1984 | Keller | 433/7 |
| 4,472,139 | 9/1984 | Rosenberg | 433/19 |
| 4,483,674 | 11/1984 | Schutz | 433/20 |

FOREIGN PATENT DOCUMENTS 1079955 12/1954 France .................... 433/19

Primary Examiner—John J. Wilson
Attorney, Agent, or Firm—Kolisch, Hartwell & Dickinson

[57] ABSTRACT

An improved means of providing adjustable relative pressure between teeth in a fixed-type formative orthodontic appliance employed to increase dental arch size in a treatment plan to overcome crowding or malocclusion is defined. The mechanism is attached to a tooth band means and includes a special screw and arm assembly which is connected to an appropriate tooth pressure-applying clasp. Adjustment of the device may be accomplished by other than a skilled practitioner due to the tooth-band-mounting of the adjustment mechanism. Incorporation of the mechanism in an orthodontic appliance permits desirable reduction in the required bulk of the appliance.

5 Claims, 7 Drawing Figures

FORMATIVE ORTHODONTIC APPLIANCE

BACKGROUND AND SUMMARY OF THE INVENTION

This invention pertains to a mechanism usable in a formative orthodontic appliance. More specifically, it pertains to an adjustably-biasing, band-mounted mechanism joining pressure-applying members of such an appliance.

Orthodontics is a specialized field of dentistry which often involves the use of special appliances to be worn in a patient's mouth and to provide corrective forces to teeth to modify their relative positions or their orientations within the mouth. These appliances, commonly known as braces, include a wide diversity of treatment approaches other than the familiar wire-and-bracket assemblies. Two such approaches, commonly used in Europe for more than 50 years and more recently in the United States, involve the use of removable appliances or functional appliances.

Removable appliances typically include molded-acrylic sections contoured to fit against the hard palate in the case of upper jaw appliances, or to fit lingually on the lower dental arch in the case of lower jaw appliances. The acrylic sections form a base from which tooth pressure applying archwires, clasps, and the like extend to contact select teeth. Adjustment of the pressures from these acrylic sections is facilitated by manufacturing each section in two or more segments. Adjacent segments are joined with guide posts consisting of a pair of hollow cylinders in one segment and mated pistons in the other segment. An expansion screw assembly installed between the guide posts provides the necessary adjustment. An adjustment is usually made by first removing the acrylic section from the patient's mouth and then turning the expansion screw to change the appliance pressure as desired.

Functional appliances are usually more complex than removable appliances and are employed to correct upper and lower jaw relative positions as well as to modify tooth positions. These appliances also may include molded-acrylic sections, screws, wires, and clasps similar to removable appliances.

In typical orthodontic practice, treatment consists of installing an appliance in the patient's mouth and then making periodic adjustments to the appliance over a period of months, or even years, gradually to correct the condition under treatment. Appliances are categorized, inter alia, as being either fixed or removable. A fixed appliance is designed to be worn continuously by the patient and should be removed by the orthodontist only. A removable appliance is designed so that the patient may, himself or herself, remove all or part of the appliance to facilitate oral hygiene, to provide periodic respites from the treatment, or to make adjustments to the appliance.

Other forms of orthodontic appliances are available that utilize metallic tooth bands to which bracket structures and archwires are attached. One embodiment of prior art, as disclosed in U.S. Pat. No. 4,468,196, issued to Keller on Aug. 28, 1984, provides a tooth-pressure-applying mechanism in the form of an archwire attached to a tooth band with adjustably-biased coil spring means. As with other prior art devices, the archwire assembly of this device must be removed in order to make an adjustment thereto.

It is therefore a general object of the invention to provide access to the tooth pressure adjustment such that the adjustment may be made while the appliance is in place in the patient's mouth.

Another object of the invention is to reduce the bulk of the appliance required for a given treatment plan so that the appliance is not physically distracting and does not impair normal speech or oral hygiene.

A further object is to provide a fixed orthodontic appliance to be worn continuously, thereby reducing overall treatment time, and to eliminate, as a factor in treatment, patient cooperation in following a schedule having periodic installation intervals.

These and other objects and advantages which are attained by the invention will become manifest as the description which now follows is read in conjunction with the accompanying drawings.

DETAILED DESCRIPTION OF THE PREFERRED EMBODIMENT

An adjustably-biasing band-means-mounted mechanism constructed in accordance with the present invention may be incorporated as part of a formative orthodontic appliance either designed to be installed on a patient's upper jaw or a patient's lower jaw. Although the upper jaw appliance is considerably different than the lower jaw appliance, the mechanism is substantially the same for either configuration; accordingly, a detailed description is provided for the mechanism as incorporated on a lower jaw appliance after the following general overview of both appliances. Operation of mechanisms on both appliances will then be described.

Figure 1:
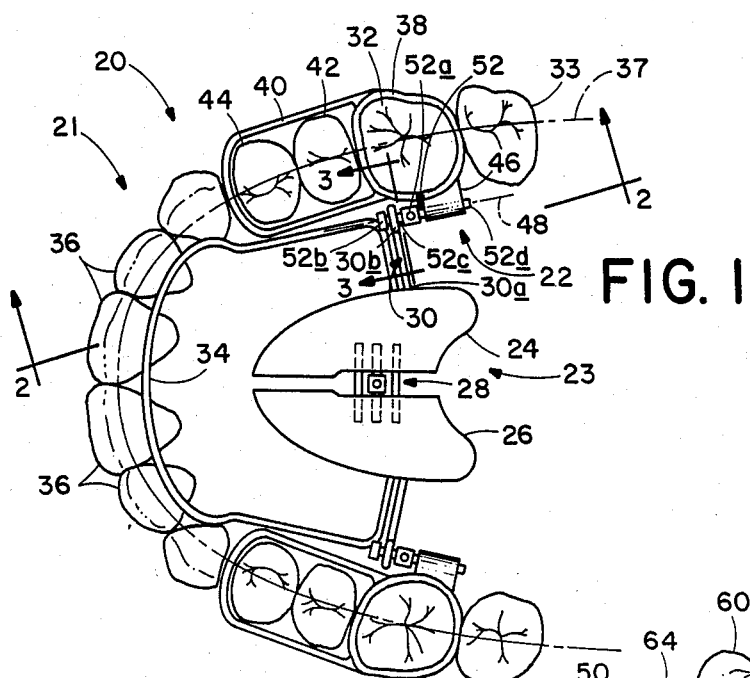
FIG. 1 is a plan view of a mechanism made according to the invention as part of an appliance installed on an upper dental arch as seen from below.

Referring to the drawings, specifically to FIG. 1, a formative orthodontic appliance, as seen from below, is shown generally at 20 installed on an upper jaw dentition, shown generally at 21. Inasmuch as this appliance consists essentially of two mirror-like halves with corresponding construction and operation, the following description will reference components on only one side of the appliance. Appliance 20 includes a mechanism, indicated generally at 22, constructed in accordance with the present invention.

Figure 2:
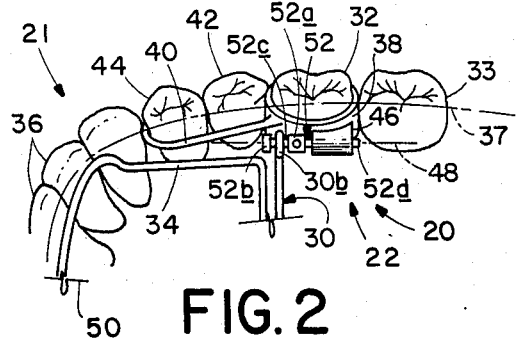
FIG. 2 is a perspective view taken generally along the line 2—2 in FIG. 1.
Figure 3:
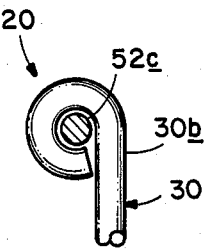
FIG. 3 is a detail enlarged cross section of the mechanism taken generally along the line 3—3 in FIG. 1.

Referring now also to FIGS. 2 and 3, a palate-nestled acrylic section, indicated generally at 23, is also included in appliance 20. This section comprises two segments 24, 26 adjoined to one another by an expansion adjustment assembly 28. The acrylic section is contoured to the wearer's hard palate and is held in place by an arm 30 which is fixedly adjoined to segment 24 at what is referred to as a first end 30a of the arm. Arm 30 generally follows the transversal contour of the hard palate and forms a loop 30b at its end lingually near a first molar 32. Also adjoined to segment 24 is a dental archwire 34 which extends from the segment adjacently and parallel to arm 30 to the gum line. It then bends sharply and extends generally anteriorly toward the lingual surfaces of incisors 36 where an incisor-contacting arcuate section is formed which follows generally parallel to an upper dental arch 37.

Referring specifically to FIGS. 1 and 2, molar 32 is seen to be encircled by a band 38 which is formed to the outside surface of molar 32 and cemented thereto. Fixedly adjoined to band 38 is a clasp 40 which extends anteriorly and forms a loop around adjacent premolars 42 and 44. A generally cylindrical body 46 is attached lingually to band 38 and extends along a longitudinal axis 48 which is generally parallel to dental arch 37. Body 46 contains a threaded bore along longitudinal axis 48 into which a mating screw portion 52d of an adjustment pin 52 is inserted. Pin 52 is also referred to as adjustable joining means. The anterior end of pin 52, as oriented in operative position, includes a spool-like section comprising spaced-apart coaxial collars 52a, 52b separated by an intermediate portion 52c. Posterior collar 52a includes two diametric holes perpendicular to one another and to longitudinal axis 48. These holes will be described further as part of the lower appliance discussed hereinafter. Intermediate portion 52c rotatably retains loop 30b of arm 30 as shown in FIG. 3.

The preferred embodiment of the instant invention as part of a lower jaw formative orthodontic appliance will now be described. As before, only one-half of the appliance will be discussed due to the characteristic mirror-image design of the appliance.

Figure 4:
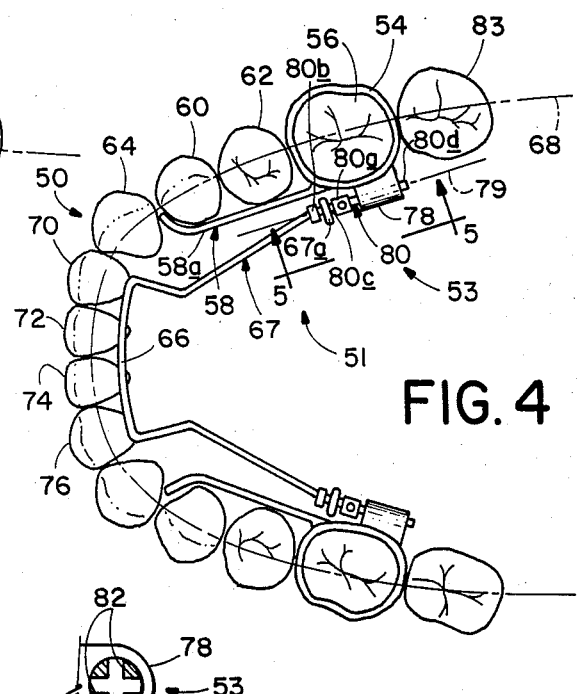
FIG. 4 is a plan view of the mechanism as part of an appliance installed on a lower dental arch as seen from above.

A formative orthodontic appliance, as seen from above, installed on a lower jaw dentition 50 is shown generally at 51 in FIG. 4. Appliance 51 includes a mechanism, indicated generally at 53, constructed in accordance with the present invention.

A band 54 is attached and cemented to a first molar 56. Fixedly attached to band 54 is a clasp 58 which extends anteriorly and lingually along the gum line past premolars 60, 62 and arches buccally at its anterior end 58a into the interproximal space of premolar 60 and a canine 64. An archwire 66 extends transversally and generally parallel to a dental arch 68, lingually contacting incisors 70, 72, 74, 76. At incisor 70, the archwire bends posteriorly orthogonal to the dental arch and adjoins to an arm 67. The arm extends sagittally and forms a loop 67a at its posterior end, as shown.

Figure 7:
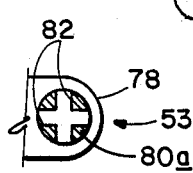
FIG. 7 is a cross section taken generally along the line 7—7 in FIG. 5.
Figure 5:
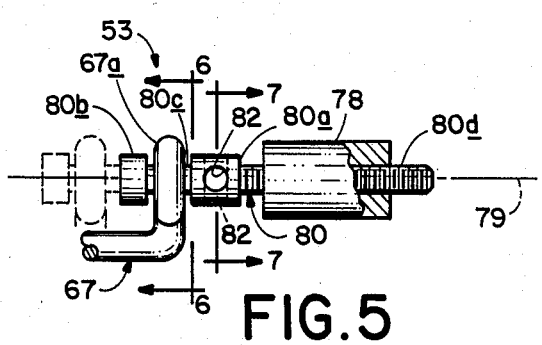
FIG. 5 is an enlarged section taken generally along the line 5—5 in FIG. 4 detailing the mechanism as configured for incorporation in a lower dental arch appliance.
Figure 6:
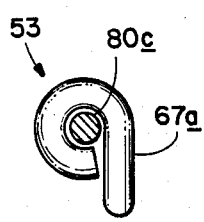
FIG. 6 is a cross section taken generally along the line 6—6 in FIG. 5.

Referring now to FIGS. 4 and 5, mechanism 53, similar to mechanism 22, is seen to include a body 78 which is disposed along a longitudinal axis 79 and contains a threaded bore. The body is fixedly attached to the lingual side of band 54. A screw portion 80d of an adjustment pin 80 is inserted into body 78. Affixed anteriorly to screw portion 80d is a spool-like section comprising collars 80a, 80b and an intermediate section 80c. Body 78 and pin 80 on the lower jaw appliance are identical in construction to body 46 and pin 52 on the upper jaw appliance, as shown in FIGS. 1 and 2. Arm 30, shown in FIGS. 1, 2, and 3, on the upper appliance, serves an analogous function to arm 67, shown in FIGS. 4, 5, and 6, on the lower jaw appliance. Posterior collar 80a contains two diametric holes 82 perpendicular to one another and to longitudinal axis 79 as shown in FIGS. 5 and 7. As noted earlier, pin 80 is identical to pin 52 and therefore holes 82 detailed in FIG. 7 are featured on collar 52a, as generally shown in FIGS. 1 and 2.

Operation of the Mechanism

The operation of the mechanism will now be described. It will be recalled that on a lower jaw appliance 51, the mechanism comprises body 78, pin 80, including screw portion 80d and a spool-like section with collars 80a, 80b and intermediate portion 80c, arm 67, and loop 67a as shown in FIGS. 4 and 5. For purposes of illustration, it will be assumed that the desired goal of appliance 51 is to increase dental arch size 68 at canine 64 to open a space between premolar 60 and incisor 70 in order to allow canine 64 to migrate lingually and posteriorly to a new position. The appliance shown accomplishes this result by anteriorly biasing the incisors with archwire 66, and posteriorly biasing premolar 60 and molar 56 with band 54 and clasp 58, respectively. The structure of archwire 66 and arm 67 forms a spring which is compressed generally sagittally when positioned as shown. Energy stored in the spring thus provides sagittal forces; following principles of statics, anterior force must be neutralized by opposite, hence posterior, force of equal magnitude. Anterior force applied to the incisors by archwire 66 is neutralized by an equal posterior force against the mechanism by means of arm 67 and loop 67a acting against pin 80. (For clarity in the drawings, loop 67a is shown in the middle, or neutral, position of intermediate section 80c of pin 80. In fact, in operation, loop 67a abuts collar 80a as a result of the described forces.)

The posterior force applied to pin 80 is transferred via body 78 to band 54 and first molar 56. Clasp 58 retains premolar 60 and transfers posterior force from band 54 to that premolar. Premolar 62 must follow any posterior migration of premolar 60 due to interproximal contact between the premolars. Similarly, a second molar 83 must migrate posteriorly with first molar 56. Thus, it is seen that appliance 51 posteriorly biases teeth 56, 60, 62 and 83 and anteriorly biases teeth 70, 72, 74 and 76.

Continuing to refer to FIGS. 4 and 5, mechanism 53 is seen to provide a means for varying the sagittal position of arm 67a; turning pin 80 such that it moves anteriorly increases the compression of the spring formed by archwire 66 and arm 67. From Hooke's Law, we know that force exerted by a spring varies in proportion to compression thereof within the elastic region of the spring. Therefore, the increased spring compression increases the sagittal forces to the teeth as described supra. Contrariwise, turning pin 80 such that it travels posteriorly, or into body 78, reduces the spring compression, yielding a corresponding decrease in the sagittal forces. Holes 82, as best seen in FIG. 7, provide a means for applying rotational force to adjust pin 80 via collar 80a with an external tool of the type that may be employed to adjust the expansion adjustment assembly of the acrylic section discussed previously. Adjustments to pin 80 may be made while the appliance is installed in the wearer's mouth due to the accessible location of collar 80a.

Operation of the upper jaw appliance is analogous to the operation of the lower appliance described supra. As shown in FIGS. 1 and 2, clasp 40, analogous to clasp 58 on the lower appliance, forms a loop around premolars 42 and 44. The function of this loop is similar to the function of clasp 58, that is, to retain the premolars and to transfer thereto any sagittal force from the band.

Archwire 34 is structured to form a spring analogous to the spring formed by archwire 66 and arm 67 on the lower jaw appliance. On the upper jaw appliance, posterior force from the spring, archwire 34, is applied to section 23. The arcuate anterior portion of archwire 34 provides anterior force to incisors 36.

Arm 30 is also structured to form a spring which applies posterior force via loop 30b to pin 52 and corresponding anterior force to section 23. This anterior force neutralizes the force from archwire 34 to the section. The arm also provides palatal force to section 23 to hold the section in place against the wearer's hard palate.

Adjustment of pin 52 changes the combined compression of the springs formed by archwire 34 and arm 30 and thereby provides the desired control over the pressures on the teeth involved in a treatment plan. As on the lower jaw appliance, adjustment to pin 52 may be made while the appliance is installed in the wearer's mouth due to the accessible location of collar 52a.

Changes and modifications to the preferred embodiment described herein will be apparent to those skilled in the art; these changes and modifications can be made without departing from the spirit and scope of the present invention. It is therefore intended that such changes and modifications be subsumed by the following claims.

It is claimed and desired to secure by Letters Patent:

1. In a formative orthodontic appliance having counteracting pressure-applying first and second members, the first member including band means fixedly joinable to a tooth, a mechanism for adjustably biasing the first and second members comprising:
 a body, fixedly adjoined to the band means, wherein a machine-screw-threaded bore extends into said body;
 an arm having a first end fixedly adjoined to the second member and a second end having a loop positioned adjacent said body; and
 adjustable joining means having a screw portion inserted into said bore, matingly threaded to said bore, for adjustment with respect to said body along a longitudinal axis of rotation, and a spool-like section which rotatably retains said loop.

2. The mechanism of claim 1, wherein said section contains a pair of coaxial, spaced-apart collars and an intermediate portion, extending through said loop between said collars, said collars being sized rotatably to retain said loop on said intermediate portion.

3. The mechanism of claim 2, wherein a first collar of said collars is longitudinal-axial-torque-transferringly joined to said screw portion and includes adjustment-facilitating means for facilitating the application of torque to said first collar to rotate said screw portion about the longitudinal axis.

4. The mechanism of claim 3, wherein said first collar is disposed for rotation about the longitudinal axis and said adjustment-facilitating means comprises a hole extending radially inwardly from an outer surface of said first collar.

5. In a formative orthodontic appliance having a pair of counteracting pressure-applying members and a first member of the members including band means disposed generally in a plane and fixedly joinable to a tooth, an adjustably-biasing band means-mounted mechanism comprising:
 a body, fixedly adjoined to the band means, having a machine-screw-threaded bore extending into said body along a longitudinal axis generally parallel to the plane;
 an arm having a first end fixedly adjoined to the second member of the pair of members, and a second end extending adjacently said body and including a loop; and
 adjustable joining means having a screw portion inserted into said bore, matingly threaded to said bore for adjustment with respect to said body along the longitudinal axis and a spool-like section containing a pair of coaxial, spaced-apart collars and an intermediate portion extending through said loop between said collars, said collars being sized to retain rotatably said loop on said intermediate portion, a first of said collars being disposed for rotation about the longitudinal axis, having a hole extending diametrically from a radially outer surface of said first collar and being longitudinal-axial-torque-transferringly joined to said screw portion.

* * * * *